United States Patent
Schneider et al.

[11] 4,086,364
[45] Apr. 25, 1978

[54] FUNGICIDAL 2,6-DINITRODIPHENYLETHERS

[75] Inventors: Louis Schneider, Elizabeth; David E. Graham, Westfield, both of N.J.

[73] Assignee: GAF Corporation, New York, N.Y.

[21] Appl. No.: 743,279

[22] Filed: Nov. 19, 1976

[51] Int. Cl.$^2$ .............. A61K 31/04; C07C 43/28
[52] U.S. Cl. .............................. 424/340; 260/612 R
[58] Field of Search .................. 260/612 R; 424/340

[56] References Cited
U.S. PATENT DOCUMENTS

| | | | |
|---|---|---|---|
| 3,050,440 | 8/1962 | Richter | 260/612 R X |
| 3,322,525 | 5/1967 | Martin et al. | 260/612 R X |

Primary Examiner—Bernard Helfin
Attorney, Agent, or Firm—Walter C. Kehm; Walter Katz

[57] ABSTRACT

Fungicidal 2,6-dinitrodiphenylethers having the formula:

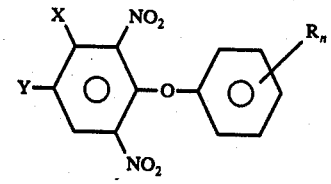

where
X is halogen,
Y is methyl or trifluoromethyl,
R is halogen or methyl, and
$n$ is 0–3.

The compounds are useful against early blight of tomatoes, bean rust, rice spot and corn rust.

19 Claims, No Drawings

FUNGICIDAL 2,6-DINITRODIPHENYLETHERS

BACKGROUND OF THE DISCLOSURE

1. Field of the Invention

This invention relates to a class of fungicides which are effective for many agricultural uses.

2. Description of the Prior Art

Diphenylether compounds are known in the art as being useful agricultural chemicals. Accordingly, it is the object of this invention to provide new diphenylethers, and particularly those which exhibit fungicidal activity.

SUMMARY OF THE INVENTION

The present invention provides fungicidal 2,6-dinitrodiphenylethers having the formula:

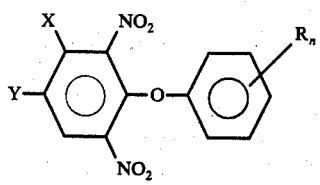

where
X is halogen,
Y is methyl or trifluoromethyl,
R is halogen or methyl, and
n is 0–3.

The compounds are useful as fungicides against early blight of tomatoes, bean rust, rice spot and corn rust.

DESCRIPTION OF THE PREFERRED EMBODIMENTS

The compounds of this invention are prepared by condensing a phenyl halide with a phenol to produce the desired diphenylether, as follows:

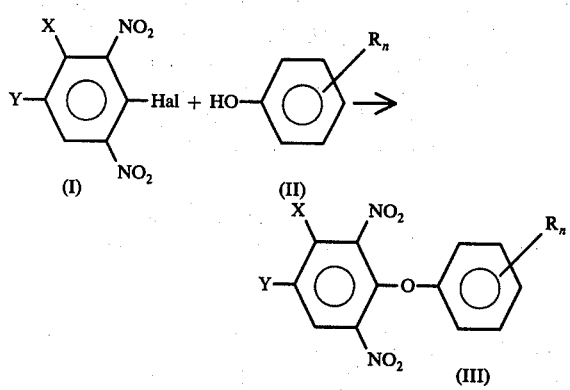

where Hal is a halogen.

The presence of the two nitro groups adjacent the halogen substituent on starting material I activates that position on the ring so condensation with the phenol, reactant II, can take place at the desired position of the benzene ring only. The reaction proceeds by nucleophilic displacement of the halogen atom by the phenoxy group to produce the desired diphenylether III.

Intermediate I is produced by dinitration of the corresponding dihalo compound IV:

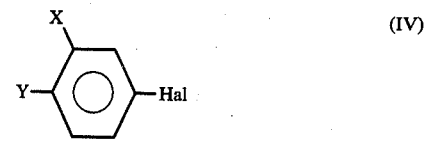

Nitration is conducted in a mixture of nitric acid to produce the dinitrated compound, as described in U.S. Pat. No. 3,586,725. Precurser IV is commercially available from the Hooker Chemical Co., Buffalo, N.Y. The phenol reactants used herein also are commercially available starting materials.

Generally, the reaction is carried out by stirring the reactants in a basic medium for an extended period of time at room temperature in a suitable solvent, such as acetone. The dilute alkali serves as an acceptor for the hydrogen-halide which is released during the reaction. Suitable alkaline compounds useful for this reaction include an alkali metal hydroxide or carbonate, such as sodium hydroxide, sodium carbonate, potassium carbonate, and the like. Upon completion of the reaction the alkali halide is filtered off and the acetone is removed by rotoevaporation. The remaining product then is recrystallized from methanol.

The compounds of the invention are useful as agricultural fungicides when applied to the soil at the rate of about 1 to 25 lbs. per acre or as a foliar spray at concentrations of about 31 to 260 ppm. They show foliar fungicidal activity against the following pathogens: early blight of tomatoes, bean rust, rice spot and corn rust, also known as alternaria solani, uromyces phaseoli, helmenthosporium oryzae and puccinia sorghi, respectively, which cause severe economic losses in tomato, bean, rice and corn crops.

The materials of the present invention may be applied to those fungus susceptible plants on site at a rate of about 1 or less to about 25 pounds per acre depending on various circumstances of the susceptibility to the fungus, the weather, the stage of growth and various other factors. The material may be applied as a dust or spray. As a dust it is more practical to extend it with diluents such as bentonite, chalk, clay, diatomaceous earth, fullers earth, mica, ground slate or any of the other usual carriers for agricultural chemicals. As a spray it may be incorporated into water as a solution. The higher molecular weight compounds may be dissolved first in a solvent, such as an alcohol, or a petroleum fraction, such as isoparaffinic hydrocarbons, naphtha or kerosene, which may act either as a cosolvent or which may be emulsified in water. For low-volume applications the material may be dissolved in a suitable solvent and fogged or sprayed without water. Usually it is desirable to incorporate emulsifying agents and other wetting agents to insure complete contact with the fungus.

Following are examples of preparation of the compounds of the invention, and are presented by way of illustration and are not intended to be limiting unless otherwise specified.

EXAMPLE 1

3-Chloro-4-Trifluoromethyl-2,6-Dinitrodiphenylether 1,3-Dichloro-2,6-dinitro-4-trifluoromethylbenzene (30.5g., 0.1 mole), phenol (9.4g., 0.1 mole), potassium carbonate (13.8g., 0.1 mole), and acetone (100 ml.) were charged into 250 cc 4-neck flask equipped with a stirrer, condenser, thermometer and a drying tube. The reaction mixture was stirred for 18 hrs. at 25°–30° C. Potassium chloride (14 g.) was filtered off and the acetone removed by rotoevaporation. The residue was crystallized from four parts of methanol yielding 14 g. (38.7%) of product, m.p. 140°–141° C., glc. 99%.

Anal. Calcd for $C_{13}H_6F_3ClN_2O_5$: N, 7.70; Cl, 9.80: Found: N, 7.77; Cl, 9.67.

EXAMPLE 2

3-Chloro-4-Trifluoromethyl 2,6-Dinitro-4'-Chlorodiphenylether 1,3-Dichloro-2,6-dinitro-4-trifluoromethylbenzene (30.5 g., 0.1 mole), p-chlorophenol (12.9 g., 0.1 mole) potassium carbonate (13.8 g., 0.1 mole), and acetone (100 ml.) were reacted and worked up as in Example 1 to yield 13 g. of product, m.p. 93.5°–94° C.

Anal. Calcd for $C_{13}H_5F_3Cl_2N_2O_5$: N, 7.03; Cl 17.83. Found: N, 6.91; Cl, 17.52.

EXAMPLE 3

3-Chloro-4-Trifluoromethyl-2,6-Dinitro-2',4'-Dichlorodiphenylether 1,3-Dichloro-2,6-dinitro-4-trifluoromethylbenzene (91.5 g., 0.3 mole), 2,4-dichlorophenol (48 g., 0.3 mole), potassium carbonate (48 g., 0.35 mole), and acetone (200 ml.) were reacted and worked up as in Example 1 to yield 69 g. of product, m.p. 151°–152° C.

Anal. Calcd for $C_{13}H_4F_3Cl_3N_2O_5$: N, 6.49; Cl, 24.7. Found: N, 6.50; Cl, 24.7.

EXAMPLE 4

3-Chloro-4-Trifluoromethyl-2,6-Dinitro-2',4',5'-Trichlorodiphenylether 1,3-Dichloro-2,6-dinitro-trifluoromethylbenzene (30.5 g., 0.1 mole), 2,4,5-trichlorophenol (19.7 g., 0.1 mole) potassium carbonate (13.8 g., 0.1 mole) and acetone (100 ml.) were reacted and worked up as in Example I to yield 21 g. of crude product which was recrystallized from methanol, m.p. 135°–136° C.

Anal. Calcd for $C_{13}H_3F_3Cl_4N_2O_5$: N, 6.02; Cl, 30.50 Found: N, 5.96; Cl, 30.55.

EXAMPLE 5

3-Chloro-4-Trifluoromethyl-2,6-Dinitro-3'-methyldiphenylether 1,3-Dichloro-2,6-dinitro-4-trifluoromethylbenzene (30.5 g., 0.1 mole), m-cresol (10.8 g., 0.1 mole) and acetone (100 ml.) were reacted and worked up as in Example I to yield 28.0 g. of product, which was recrystallized from methanol, m.p. 96°–97° C.

Anal. Calcd for $C_{14}H_8ClF_3N_2O_5$: N, 7.43; Cl, 9.42 Found: N, 7.49; Cl, 9.40.

EXAMPLE 6

3-Chloro-4-Trifluoromethyl-2,6-Dinitro-4'-Methyldiphenylether 1,3-Dichloro-2,6-dinitro-4-trifluoromethylbenzene (30.5 g., 0.1 mole), p-cresol (10.8 g., 0.1 mole) potassium carbonate (13.8 g., 0.1 mole) and acetone (100 ml.) were reacted as in Example I with an extended heating period of 64 hours at 40° C. The reaction mixture was worked up to yield 25.0 g. of product, which was recrystallized from methanol, m.p. 105°–106° C.

Anal. Calcd for $C_{14}H_8ClF_3N_2O_5$: N, 7.43; Cl, 9.42 Found: N, 7.47; Cl, 9.45.

EXAMPLE 7

3-Chloro-4-Methyl-2,6-Dinitrodiphenylether

Phenol (9.4 g. 0.1 mole), potassium carbonate (6.9 g. 0.05 mole) and xylene (150 ml.) were heated to reflux and the xylene-water azeotroped off to form the potassium phenolate. The reaction mixture was cooled to 10° C. and 2,4-dichloro-3,5-dinitrotoluene (25.1 g., 0.1 mole) was added at 25° C. After 24 hours at 100° C., the mixture was partitioned between xylene and water. The water phase was extracted with aqueous 5% potassium carbonate and the xylene removed by rotoevaporation. The crude product was crystallized from methanol to yield 10 g., m.p. 142.5°–144° C.

Anal. Calcd. for $C_{13}H_9ClN_2O_5$: N, 9.08; Cl, 11.48 Found: N, 8.82; Cl, 11.24.

EXAMPLE 8

3-Chloro-4-Trifluoromethyl-2,6-Dinitro-4'-Fluorodiphenylether 2,4-Dichloro-3,5-dinitro-4-trifluoromethylbenzene (30.5 g., 0.1 mole), 4-fluorophenol (11.2 g., 0.1 mole) potassium carbonate (13.8 g., 0.1 mole) and acetone (100 ml.) were reacted and worked up as in Example I to yield 25 g. of crude product which was recrystallized from methanol, m.p. 91°–92° C.

Anal. Calcd. for $C_{13}H_5F_4ClN_2O_5$: N, 7.36, Cl, 9.31 Found: N, 7.31; Cl, 9.48.

EXAMPLE 9

Foliage Fungicide Tests

The product of Example 1 was tested on tomato early blight as follows: Young tomato seedlings 4 to 5 weeks of age were atomized while rotating on a turntable with a suspension of the test material diluted to 125, 63 and 31 ppm. After the deposit dried, the plants were atomized with a spore suspension and incubated in a humidity cabinet at 70° to 75° F for 24 hours. Then they are held in a greenhouse until lesions appear (usually 2 to 3 days.) The severity of infection is rated on a scale of 0 (no reduction) to 10 (complete elimination of infection.) The results versus the standard Maneb, manganese ethyl bis-dithiocarbamate are as follows.

| Conc., ppm | Fungitoxicity Rating | |
|---|---|---|
| | Compound of Ex. 1. | Maneb |
| 125 | 6.5 | 6.4 |
| 62 | 6.1 | 4.8 |
| 31 | 3.4 | 0.2 |

EXAMPLE 10

The product of Example 2 was tested on bean rust as follows: Pinto beans grown in 2.5 inch pots for 9 to 12 days is sprayed while plants are rotating on a turntable with 100 ml. of a formulation at 125, 63 and 31 ppm. After the spray deposit dries, plants are placed in a moist chamber at 70° F. for 24 hours. After 7 to 9 days the severity of pustule formation is rated as in Example 9 and compared with the commercial standard Plantvax, 2,3-dihydro-5-carbanilido-6-methyl-1,4-oxathiin-4,4-dioxide.

| Conc., ppm | Fungitoxicity Rating | |
| --- | --- | --- |
| | Compound of Ex. 2 | Plantvax |
| 125 | 10 | 10 |
| 62 | 10 | 9 |
| 31 | 8.5 | 7.5 |

EXAMPLE 11

The product of Example 2 was tested on rice leaf spot as follows: Young Star Bonnet rice plants about 2 weeks old growing in 2.5 inch pot are sprayed while rotating with a suspension containing 125, 62 and 31 ppm of a material. After the spray deposit dries, the plants are atomixed with a conidial suspension and placed in a moist chamber at 75° F. for 24 hours to facilitate infection. After discrete lesions appear in the unprotected controls (2 days), the infection is rated versus the commercial standard Maneb.

| Conc., ppm | Fungitoxicity Rating | |
| --- | --- | --- |
| | Compound of Ex. 2 | Maneb |
| 125 | 5.0 | 6.5 |
| 62 | 4.0 | 5.5 |
| 31 | 3.0 | 3.0 |

EXAMPLE 12

The product of Example 1 was tested on corn rust as follows: Young corn plants were treated as in Example 11 and rated versus the standard Plantvax.

| Conc., ppm | Fungitoxicity Rating | |
| --- | --- | --- |
| | Compound of Ex. 1 | Plantvax |
| 200 | 9.0 | 8.5 |
| 50.0 | 8.5 | 6.3 |
| 12.5 | 5.5 | 2.5 |
| 6.3 | 6.5 | 0.0 |

EXAMPLE 13

Similarly, the compounds of Examples 3–8 showed fungicidal activity in fungicidal screening tests.

What is claimed is:

1. Fungicidal 2,6-dinitrodiphenylethers having the formula:

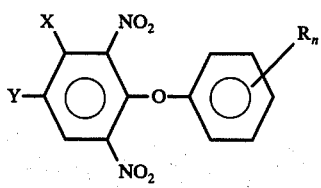

where
X is halogen,
Y is methyl or trifluoromethyl,
R is halogen or methyl, and
n is 0–3.

2. 3-Chloro-4-Trifluoromethyl-2,6-Dinitrodiphenylether.

3. 3-Chloro-4-Trifluoromethyl -2,6-Dinitro-4'-Chlorodiphenylether.

4. 3-Chloro-4-Trifluoromethyl-2,6-Dinitro-2',4'-Dichlorodiphenylether.

5. 3-Chloro-4-Trifluoromethyl-2,6-Dinitro-2',4',5'-Trichlorodiphenylether.

6. 3-Chloro-4-Trifluoromethyl-2,6-Dinitro-3'-methyldiphenylether.

7. 3-Chloro-4-Trifluoromethyl-2,6-Dinitro-4'-Methyldiphenylether.

8. 3-Chloro-4-Methyl-2,6-Dinitrodiphenylether.

9. 3-Chloro-4-Trifluoromethyl-2,6-Dinitro-4'-Fluorodiphenylether.

10. A method of controlling fungus growth in plants comprising applying thereto a fungicidally effective amount of a compound having the formula:

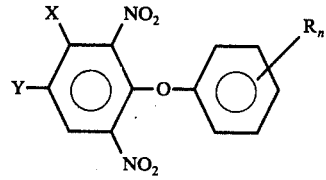

where
X is halogen,
Y is methyl or trifluoromethyl,
R is halogen or methyl, and
n is 0–3.

11. A method according to claim 10 in which said compound is 3-Chloro-4-Trifluoromethyl-2,6-Dinitrodiphenylether.

12. A method according to claim 10 in which said compound is 3-Chloro-4-Trifluoromethyl 2,6-Dinitro-4'-chlorodiphenylether.

13. A method according to claim 10 in which said compound is 3-Chloro-4-Trifluoromethyl-2,6-Dinitro-2',4'-Dichlorodiphenylether.

14. A method according to claim 10 in which said compound is 3-Chloro-4-Trifluoromethyl-2,6-Dinitro-2',4',5'-Trichlorodiphenylether.

15. A method according to claim 10 in which said compound is 3-Chloro-4-Trifluoromethyl-2,6-Dinitro-3'-methyldiphenylether.

16. A method according to claim 10 in which said compound is 3-Chloro-4-Trifluoromethyl-2,6-Dinitro-4'-Methyldiphenylether.

17. A method according to claim 10 in which said compound is 3-Chloro-4-Methyl-2,6-Dinitrodiphenylether.

18. A method according to claim 10 in which said compound is 3-Chloro-4-Trifluoromethyl-2,6-Dinitro-4'-Fluorodiphenylether.

19. A fungicidal composition of matter comprising:
(a) A fungicidally effective amount of a compound having the formula:

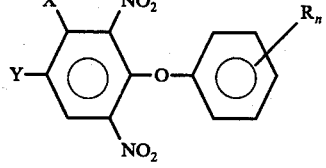

where
X is halogen,
Y is methyl or trifluoromethyl,
R is halogen or methyl, and
n is 0–3, and
(b) an inert carrier.

* * * * *